United States Patent [19]

Winkler

[11] 4,120,866

[45] Oct. 17, 1978

[54] PREPARATION OF ARYLSULPHONIUM SALTS

[75] Inventor: Adolf Winkler, Leverkusen, Germany

[73] Assignee: Bayer Aktiengesellschaft, Leverkusen, Germany

[21] Appl. No.: 833,927

[22] Filed: Sep. 16, 1977

[30] Foreign Application Priority Data

Oct. 2, 1976 [DE] Fed. Rep. of Germany ....... 2644591

[51] Int. Cl.² ............................................. C07D 209/82
[52] U.S. Cl. .................................. 260/315; 260/329 R; 260/346.71; 260/607 B
[58] Field of Search ............... 260/607 B, 346.71, 315, 260/609 E, 609 F, 329 R

[56] References Cited

U.S. PATENT DOCUMENTS

| 3,732,317 | 5/1973 | Pilgram et al. | 260/607 B |
| 3,758,594 | 9/1973 | Campen et al. | 260/607 B |

OTHER PUBLICATIONS

*Topics in Sulfur Chemistry*, "Sulfur Containing Cations," p. 36, J. P. Marino (A. Senning, editor), (1976), Thieme Publishers, Germany.

*Primary Examiner*—Lewis Gotts
*Assistant Examiner*—Molly C. Eakin
*Attorney, Agent, or Firm*—Burgess, Dinklage & Sprung

[57] ABSTRACT

A process for the production of an arylsulphonium salt, comprising reacting an aromatic compound of the formula $$Ar-H$$

in which Ar is an aromatic radical with a sulphoxide of the formula

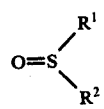

in which $R^1$ and $R^2$ each independently is an aliphatic or aromatic radical or, together, a divalent radical, in the presence of hydrogen fluoride. The products are known and can be converted to arylthioethers which are intermediates for other known syntheses.

9 Claims, No Drawings

PREPARATION OF ARYLSULPHONIUM SALTS

The invention relates to a process for the preparation of arylsulphonium salts by reacting aromatic compounds with sulphoxides in the presence of hydrofluoric acid.

It has been found that arylsulphonium salts are obtained when aromatic compounds of the formula

Ar-H     (I)

in which Ar denotes an optionally substituted aromatic radical, which can also contain one or more heteroatoms, are reacted with a sulphoxide of the formula

(II)

in which $R_1$ and $R_2$ are identical or different and denote an optionally substituted aliphatic or aromatic hydrocarbon radical or, together, an optionally substituted divalent hydrocarbon radical, in the presence of hydrogen fluoride.

Possible optionally substituted aromatic radicals (Ar) are mononuclear or polynuclear carbocyclic and heterocyclic aromatic radicals, preferably the phenyl and naphthyl radical.

Possible hetero-atoms in the heterocyclic aromatic radicals are, in particular, oxygen, nitrogen and sulphur.

Optionally substituted aliphatic radicals which may be mentioned are preferably straight-chain or branched alkyl radicals with up to 12, in particular up to 6, carbon atoms, such as methyl, ethyl, propyl and isopropyl; and furthermore butyl, isobutyl, tert.-butyl and the isomeric pentyl and hexyl radicals.

Optionally substituted cycloaliphatic radicals which may be mentioned are preferably those with 4 to 8 carbon atoms, in particular the cyclopentyl and cyclohexyl radical.

Optionally substituted aromatic radicals which may be mentioned are those with 6 to 20 carbon atoms, in particular the phenyl, naphthyl and anthranyl radical.

Optionally substituted divalent hydrocarbon radicals, which the radicals $R^1$ and $R^2$ can together form, which may be mentioned are radicals containing 3 to 6 carbon atoms in the chain, preferably the tetramethylene radical.

Compounds of the formula

(III)

in which $R^3$ and $R^4$ are identical or different and represent the hydroxyl group or optionally substituted alkyl, aryl, alkoxy, aroxy, alkylthio or arylthio radicals, $R^5$ represents halogen or an optionally substituted alkyl radical and p and q are identical or different and denote one of the numerals 0, 1 or 2, wherein in the case where p and/or q denote the numeral 2, the two radicals $R^4$ and/or $R^5$ can each have a different meaning and wherein $R^3$ and an adjacent radical $R^4$ and/or, in each case, two adjacent radicals $R^4$ and/or $R^5$ can also together form, conjointly with the carbon atoms substituted by them, an optionally substituted fused, cycloaliphatic or aromatic 5-membered or 6-membered ring, are preferably used as the starting compounds of the formula (I).

Possible alkyl radicals are straight-chain and branched, saturated, aliphatic radicals with up to 18, preferably up to 12 and especially with 1 to 4, carbon atoms.

Possible aryl radicals are those with 6 to 20 carbon atoms, in particular the phenyl, naphthyl and anthranyl radical.

The alkyl and aryl radicals of the alkoxy, aroxy, alkylthio and arylthio radicals have the abovementioned scope of meaning.

Fluorine, chlorine, bromine and iodine, especially chlorine, are possible as halogen.

Possible substituents of the aromatic radicals, aryl, aroxy and arylthio groups are preferably the hydroxyl group, halogen, alkyl and alkoxy, alkylthio, aroxy and arylthio groups.

Compounds of the formulae (I) and (III) which may be mentioned in particular are: toluene and o-, m- and p-xylene; naphthalene, α- and β-alkylnaphthalenes and dialkylnaphthalenes, in particular the methyl and ethyl compounds, and anthracene; diphenyl, diphenylmethane, tetralin and indane; phenol, o-, m- and p-cresol, butylphenol and the xylenols; resorcinol, pyrocatechol and hydroquinone; α- and β-naphthol; mono-alkyl and di-alkylphenol ethers, such as anisole, hydroquinonedimethyl ether, pyrocatechol monomethyl ether and α- and β-methoxynaphthalene; the corresponding thioethers, such as thioanisole and 4-hydroxythioanisole; halogenophenols, such as o-, m- and p-chlorophenol; and furthermore diphenyl ether, dibenzofurane, carbazole, acenaphthene, fluorene, cumene, mesitylene and o-, m- and p-cymene.

Dimethylsulphoxide, diethylsulphoxide, methylphenylsulphoxide, (p-tolyl)-methyl-sulphoxide, (p-anisyl)-methylsulphoxide, (p-tert.-butyl-phenyl)-ethylsulphoxide and tetrahydrothiophenoxide may be mentioned as preferred starting compounds of the formula (II).

Hydrogen fluoride is employed as such in either the gaseous or liquid state or as an aqueous solution containing at least 80% by weight of hydrogen fluoride.

Since, according to the reaction equation

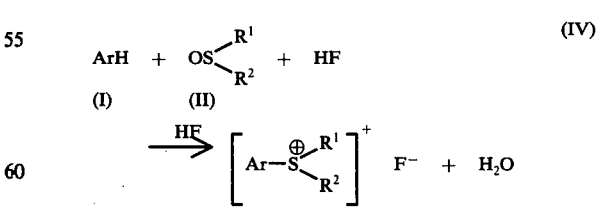

(IV)

in which Ar, $R^1$ and $R^2$ have the meaning indicated above, per mol of starting compound of the formula (I) 1 mol of hydrogen fluoride is consumed for the formation of the sulphonium salt of the formula (IV) and 1 mol of water is formed, it is advantageous when the hydrofluoric acid employed has a content of hydrogen fluoride of at least about 90% by weight, preferably at least about 95% by weight; commercially available anhydrous hydrofluoric acid is particularly advantageously used.

In the process according to the invention the hydrofluoric acid serves simultaneously as a reactant, condensing agent and reaction medium. Thus up to about 50, preferably about 2–10 and especially about 2–5, parts by weight of hydrofluoric acid are used per 1 part by weight of the starting compound (I) or (III). It is also possible to use larger amounts of hydrofluoric acid.

In general, the aromatic starting compound of the formula (I) and the sulphoxide of the formula (II) are employed in the stoichiometric ratio of 1 mol:1mol.

However, it can also be advantageous to employ the aromatic starting compound (I) in excess, when, for example, it is more easily accessible or in order thereby to suppress polysubstitution by the sulphonium grouping.

Furthermore, when readily available isomer mixtures are used, for example xylenes or cresols, it can be advantageous to employ these in an excess so that a reaction of the sulphoxide (II) takes place only with the most reactive isomer.

However, it is also possible to use the sulphoxide of the formula (II) in excess. This is advantageously done if not only one but two or more sulphonium groups are to be introduced into the aromatic compounds of the formula (I); in this case, the correspondingly larger chosen amount of hydrofluoric acid is to be used simultaneously.

In general, the sequence of bringing together the reactants is not critical. However, from practical considerations it is not advantageous initially to bring together the sulphoxide of the formula (II) and hydrofluoric acid since, in general, in this procedure a marked exothermic effect occurs which, because of the low boiling point of the hydrogen fluoride, must be removed by cooling.

Appropriately, hydrofluoric acid and the aromatic compound of the formula (I) are first mixed.

The process according to the invention is advantageously carried out by mixing the hydrofluoric acid and aromatic compound of the formula (I) at temperatures below the boiling point of hydrogen fluoride of 19° C., preferably between about 0° and −80° C., in particular between about 0° and 31 20° C., and to introduce the sulphoxide of the formula (II) slowly, or add it dropwise, into this solution or suspension, while mixing thoroughly, care being taken, by cooling, that the temperature of the mixture remains within the limits indicated. After the components have been mixed, virtually no exothermic effect occurs; the further reaction can be carried out under normal pressure at room temperature.

However, it can also be advantageous to bring the further reaction to completion in a closed vessel under the autogenous pressure of the reaction mixture at elevated temperature.

In this procedure, the reaction temperature is between about 0° and 150° C., preferably between about 20° and 100° C.; the reaction is particularly advantageously brought to conclusion in the temperature range between about 40° and 70° C.

It is also possible to initially introduce the reactants of the formulae (I) and (II) in the closed vessel at temperatures above about 0° C. and also have room temperature and to pass in hydrogen fluoride at a higher temperature, optionally at the chosen reaction temperature, under pressure or to pump hydrofluoric acid in.

It is, of course, also possible to initially introduce liquid hydrogen fluoride and, at a temperature below its boiling point and under normal pressure, to add the two reactants, together or individually in any desired sequence. This bringing together can, of course, also be carried out at a higher temperature up to the chosen reaction temperature; in this case it must be ensured that the initially introduced hydrogen fluoride cannot escape, that is to say the procedure is to be carried out under reflux or increased pressure.

A mixture of hydrogen fluoride and one reactant can also be initially introduced and the other subsequently added.

The sequence of bringing together the reactants and the temperature settings for the procedure up to the conversion at the reaction temperature can in themselves be freely chosen; the preferred embodiments described above result from practical considerations, as mentioned, for example because of the low boiling point of the hydrogen fluoride.

The reaction time in the process according to the invention depends on the nature of the starting compounds of the formulae (I) and (II), so that it cannot be given generally. It can be determined by a few preliminary experiments; exceeding the necessary reaction time is not harmful.

In general, after the reaction has ended excess hydrofluoric acid is separated off by distillation, for example with the aid of a column, a thin film evaporator or a falling film evaporator. When the excess of hydrofluoric acid is sufficient, distilling off the hydrofluoric acid can optionally already take place during this reaction or, in other words, the subsequent reaction after the reactants have been brought together can be combined with the distilling off of excess hydrofluoric acid. It is also possible, in the customary manner, to dilute the entire reaction mixture with water and either to precipitate the sulphonium ion from this aqueous solution, for example as the perchlorate by adding perchloric acid or a water-soluble perchlorate, or to evaporate the aqueous solution, if appropriate after extracting excess or unreacted organic starting compounds and removing excess hydrofluoric acid as a sparingly soluble fluoride.

The reaction product which remains as the distillation residue after distilling off the hydrofluoric acid can already be so pure that it is obtained as a crystalline salt and can be further used as such.

Any starting material of the compounds (I) or (II) which may be employed in excess or may be unreacted can also be separated off in a known manner, for example by distillation.

In general, however, the residue obtained after distilling off the excess hydrofluoric acid is dissolved in a diluent, preferably water. Any excess or unreacted starting material which may still be present can then be recovered by known processes, such as, for example, extraction with an organic solvent. Hydrofluoric acid still remaining in the residue can likewise be optionally precipitated out of the solution with suitable precipitating agents, such as calcium carbonate, calcium oxide or calcium hydroxide, in a known manner.

From the solution of the resulting sulphonium salt, this can also be obtained in the customary manner by crystallization.

If a phenol of the general formula (III) (R$_3$=OH) is used, sulphonium hydroxides or internalsulphonium salts of the general formulae

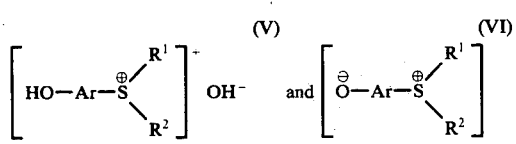

in which Ar, R$^1$ and R$^2$ have the meanings indicated above, can be obtained by precipitating the fluoride ion from the solution of the reaction product.

Arylsulphonium salts with other anions can be prepared from the arylsulphonium fluorides of the general formula (IV) by double decompositon in a known manner, for example the sparingly soluble sulphonium perchlorates are obtained by reaction with perchloric acid; by reacting the internalsulphonium phenolates of the formula (VI) with acids, the corresponding sulphonium salts are likewise obtained.

Compared with known processes for the preparation of sulphonium salts, the process according to the invention is distinguished by the fact that the condensing agent and solvent used is hydrofluoric acid which, because of its low boiling point, can be particularly easily recovered by simple distillation, so that no problems of environmental protection arise since the handling of anhydrous and highly concentrated hydrofluoric acid on a large industrial scale is a problem which has been solved. Any separation of the fluoride ion from effluents obtained also presents no difficulties since it can be separated out, as is known, as sparingly soluble calcium fluoride.

Sulphonium salts which can be obtained by the process according to the invention are valuable intermediate products as alkylating agents.

In particular, corresponding arylthio-ethers can be obtained from them by known processes, which in turn are intermediate products for the preparation of pharmaceuticals, plant protection agents and dyestuffs.

For example, alkylmercaptophenols are starting compounds for insecticidal carbamates (British patent specification No. 912,895) and dyestuffs (DT-AS (German Published Specification) No. 1,173,602; and U.S. Pat. No. 3,293,270).

Sulphonium salts themselves can be polymerized, according to U.S. Pat. No. 2,768,990, to give sulphonium anion exchangers.

Furthermore, thioether phenols, such as can be obtained from the sulphonium salts in a known manner, can be used, according to U.S. Pat. No. 3,553,163, as antiaging agents.

The invention is further described in the following illustrative examples wherein the anhydrous hydrofluoric acid used is anhydrous hydrofluoric acid of commercially available quality with a content of HF of about 99%.

When precipitation of the corresponding sulphonium perchlorate is described in the examples, it is carried out by adding a few drops of 70% strength by weight aqueous perchloric acid to a sample, having a volume of about 1 ml, of the aqueous sulphonium salt solution.

EXAMPLE 1

A mixture of 138 g (1.5 mols) of toluene and 117 g (1.5 mols) of dimethylsulphoxide is added dropwise to 500 ml of anhydrous hydrofluoric acid, while cooling with an ice/sodium chloride freezing mixture. The inhomogeneous mixture is transferred to a 1.3 l high-grade steel autoclave and stirred for 10 hours at 70° C.

Most of the hydrofluoric acid is distilled off from the resulting brown homogeneous solution from a boiling water bath, first under normal pressure and then under a waterpump vacuum.

The residue is diluted wioth water to 1.5 l, the solution is clarified with charcoal and completely neutralized hot by adding calcium carbonate incrementally and filtered hot.

p-Tolyl-dimethyl-sulphonium perchlorate of melting point 123° to 125° C. is precipitated from a sample of the filtrate on adding 70% strength aqueous perchloric acid.

150 g of potassium hydroxide are added to the main proportion of the aqueous solution of p-tolyl-dimethylsulphonium fluoride and the mixture is boiled for about 3 hours under reflux. The oily p-tolyl-methyl sulphide which has separated out is then extracted with ether in the customary manner, the ether is dried and distilled off and the residue is distilled in vacuo.

This gives 137 g (66.2% of theory) of p-tolyl-methyl sulphide of boiling point 90°–92° C./16 mm Hg.

EXAMPLES 2–12

To the amount of anhydrous hydrofluoric acid indicated in Table (I) which follows, was added dropwise an equimolar mixture of, in each case, the amount (in mols) indicated of the aromatic compound indicated and dimethylsulphoxide, while cooling with an ice/sodium chloride freezing mixture. The mixture was then transferred to a 1.3 l high-grade steel autoclave and, in each case, stirred for the reaction time indicated at the reaction temperature indicated.

Most of the excess hydrofluoric acid was then distilled off from the reaction mixture from a boiling water bath, first under normal pressure and then under a water pump vacuum.

The residue was diluted with water to 1.5 l, the solution was clarified with charcoal and completely neutralized hot with calcium carbonate and then filtered.

The corresponding sulphonium perchlorate was precipitated from a sample of the filtrate; its melting point is indicated in Table (I).

About twice the molar amount of potassium hydroxide, relative to the sulphonium salt, was added to the filtrate and the mixture was boiled for about 3 hours under reflux. The oily sulphide which separated out was then extracted with ether and isolated from the ether extract, analogously to Example 1. The boiling point or melting point as well as the yield are also indicated in Table I which follows.

The resulting sulphonium perchlorate as well as the corresponding methyl thioether are identified in the table by their formulae and those of the radicals R$^6$ and R$^7$.

Table I $$\left[\begin{array}{c} R^6 \\ \\ R^7 \end{array}\!\!\!\!\!\!\!\!\!\!\!\!\!\!\!\!\!\!\! \bigcirc\!\!\!-\!\!\!\overset{\oplus}{S}\!\!<\!\!\!\begin{array}{c}CH_3 \\ CH_3\end{array}\right]^+ ClO_4^- \qquad \begin{array}{c}R^{6'} \\ \\ R^{7'}\end{array}\!\!\!\!\!\!\!\!\!\!\!\!\!\!\!\!\!\!\! \bigcirc\!\!\!-\!\!\!S\!\!-\!\!CH_3$$

| Ex. No. | Starting Compound | mols | HF ml | Reaction time hours | temperature °C | Melting point °C | R⁶ | R⁷ | Yield % of theory | Melting point or boiling point °C(mm Hg) |
|---|---|---|---|---|---|---|---|---|---|---|
| 2 | p-xylene | 1.0 | 300 | 65 | 20 | 158–159 | 2-methyl | 5-methyl | 77 | 70(1.5) |
| 3 | m-xylene | 1.75 | 500 | 10 | 70 | 165 | 2-methyl | 4-methyl | 68.5 | 112(17) |
| 4 | o-xylene | 1.75 | 500 | 10 | 60 | 163–165 | 3-methyl | 4-methyl | 71.5 | 113(15) |
| 5 | anisole | 1.0 | 300 | 16 | 20 | 80–82 | 4-methoxy | — | 70.2 | 136–137(30) |
| 6 | 4-methoxy-toluene | 1.5 | 500 | 10 | 70 | 122–124 | 2-methoxy | 5-methyl | 87 | 116(2.5) |
| 7 | 3-methoxy-toluene | 1.5 | 500 | 10 | 50 | 157–159 | 4-methoxy | 2-methyl | 88.5 | 113(2.5) |
| 8 | 2-methoxy-toluene | 1.5 | 500 | 10 | 60 | 88–90 | 4-methoxy | 3-methyl | 77 | 137(20) |
| 9 | 1,4-dimethoxybenzene | 1.0 | 400 | 65 | 20 | 149–151 | 2-methoxy | 5-methoxy | 78.5 | 118(1.5) |
| 10 | 1,3-dimethoxybenzene | 1.0 | 300 | 16 | 20 | 168–169 | 2-methoxy | 4-methoxy | 50 | 37–39 143(3.5) |
| 11 | diphenyl | 1.3 | 500 | 10 | 70 | 220 | 4-phenyl | — | 73 | 106–107 |
| 12 | tetralin | 1.5 | 500 | 10 | 60 | 161–162 | 3,4-tetramethylene | | 74.5 | 122–125 (1.5) |

EXAMPLE 13

A mixture of 138 g (1.0 mol) of pyrocatechol dimethyl ether and 78 g (1.0 mol) of dimethylsulphoxide is added dropwise to 300 ml of anhydrous hydrofluoric acid at −10° C., while stirring. The mixture is then further stirred for 16 hours at room temperature (about 20° C.).

A sample which is taken is soluble in water to give a clear solution and (3,4-dimethoxyphenyl)-dimethyl-sulphonium perchlorate of melting point 168°–169° C. precipitates on adding perchloric acid.

The hydrofluoric acid is distilled off from the reaction solution from a boiling water bath, first under normal pressure and then under a waterpump vacuum, and the residue is diluted with water to 1.5 l. The aqueous solution is clarified with charcoal and completely neutralized hot by adding calcium carbonate incrementally and then filtered.

Water is distilled off from the filtrate under normal pressure and the residue is then heated to 140°–150° C. in an oil bath until no more methyl fluoride is given off.

This gives 165 g of a crude product with a (3,4-dimethoxyphenyl)-methyl sulphide content of 97.2%, corresponding to a yield of 87% of theory.

During the distillation, the pure compound distils at 140° C./3 mm Hg; the distillate crystallizes spontaneously: melting point 29°–30° C.

EXAMPLE 14

A mixture of 170 g (1.0 mol) of diphenyl ether and 78 g of dimethylsulphoxide is added dropwise to 400 ml of anhydrous hydrofluoric acid in the course of 4 hours at about 0° C., while stirring. The mixture is then further stirred for 18 hours at room temperature (about 20° C.).

The hydrofluoric acid is then distilled off and the residue which remains is diluted with water to 1.5 l and the solution is neutralized with aqueous potassium hydroxide solution.

100 g of potassium hydroxide are then added and the mixture is heated to the boil for about 3 hours under reflux.

The reaction product which separates out during this procedure is isolated by extracting with methylene chloride; this gives 185 g of crude product which contains 60.4% of diphenyl ether, corresponding to a conversion of 34.2%, and 37.8% of 4-methylmercaptodiphenyl ether, which corresponds to a yield of 32.4% of theory, and 95% with respect to the conversion.

4-Methylmercaptodiphenyl ether is obtained in the pure form by distillation: boiling point 150° C./1.5 mm Hg.

EXAMPLE 15

127.5 g (0.75 mol) of diphenyl ether was added dropwise, with 117 g (1.5 mols) of dimethylsulphoxide, to 500 ml of anhydrous hydrofluoric acid at about 0° C., while stirring, and the mixture was then stirred for 10 hours at 70° C.

A sample of the pale red homogeneous solution, in which the reaction had ended, diluted with water gave diphenyl ether 4,4'-bis-dimethylsulphonium fluoborate of melting point 120°–123° C. on adding fluoboric acid.

The solution was worked up according to Example 1 to give 162 g of crude product which contained 9.6% of 4-methylmercaptodiphenyl ether and 87.1% of 4,4'-bis-methylmercaptodiphenyl ether.

The yield of 4,4'-bis-methylmercapto-diphenyl ether corresponds to 72% of theory; melting point 79°–80° C. (from hexane).

EXAMPLE 16

18.9 g (0.15 mol) of 3-fluoroanisole and 12 g of dimethylsulphoxide were filled into a 100 ml high-grade steel autoclave and frozen, while cooling with acetone/dry ice; 65 g of anhydrous hydrofluoric acid were then added. The reaction mixture was then stirred for 4½ hours at 60° C. Hydrogen fluoride was allowed to evaporate from the yellow reaction solution at 60° C.

A sample of the residue, diluted with water, gave a precipitate of (4-methoxy-2-fluoro-phenyl)-dimethylsulphonium perchlorate of melting point 166°–168° C. by adding 70% strength aqueous perchloric acid.

The residue was taken up in 250 ml of water, the solution was neutralized with aqueous potassium hydroxide solution and a further 25 g of potassium hydroxide were added and the mixture was then heated to the boil for 3 hours under reflux.

The reaction mixture was then extracted with ether and the ether extract gave 15 g (58% of theory) of a crude product which consists of 2 isomeric methylmercapto-3-fluoro-anisoles in the ratio of about 1:1, which cannot be separated by distillation; boiling point 85°–89° C./1 mm Hg.

EXAMPLE 17

19.9 g (0.1 mol) of 4-fluoro-3'-methyl-diphenyl ether are mixed with 8 g of dimethylsulphoxide and 50 ml of anhydrous hydrofluoric acid are poured over the mixture, while cooling with acetone/dry ice. The mixture is then stirred for 2 hours in a 100 ml autoclave at 60° C.

4'-Fluoro-3-methyl-4-dimethylsulphonium diphenyl ether perchlorate of melting point 128°–130° C. is precipitated from a sample of the aqueous solution on adding 70% strength aqueous perchloric acid.

Hydrogen fluoride is allowed to evaporate from the reaction solution, the evaporation residue is taken up in 250 ml of water and the solution is neutralized with aqueous potassium hydroxide solution and heated, after adding 25 g of potassium hydroxide, for 3 hours under reflux.

The solution is then extracted with ether.

Distillation of the ether extract under a waterpump vacuum gives 2.0 g. (about 10%) of unreacted starting material as the distillate and 16 g of a crude product, as the residue, which contains 92% of 4-methylmercapto-3-methyl-4'-fluorodiphenyl ether, corresponding to a yield of 58% of theory.

The crude product still contains 7.5% of an isomer which has not been identified.

This isomer cannot be separated off, even by distillation at 154° C./1 mm Hg.

EXAMPLE 18

281 g (1.5 mols) of 4-bromo-anisole are reacted with 117 g of dimethylsulphoxide in 500 ml of anhydrous hydrofluoric acid for 10 hours at 60° C.

Excess hydrofluoric acid is then separated off, the residue is made up to 1.5 liters with water and, after neutralization with aqueous potassium hydroxide solution, 150 g of KOH are added to the mixture and this is heated to the boil for 3 hours.

The organic constituents are then extracted with ether. From the ether extract, a total of 278 g of a crude product are contained which has the following composition according to analysis by gas chromatography: 12.5% of 4-bromo-anisole, 39.5% of 2,4-dibromo-anisole; melting point 61°–63° C., 26.0% of 4-methylmercapto-anisole and 22.0% of 2-methylmercapto-4-bromo-anisole.

Distillation under reduced pressure gives, in the boiling range 172°–177° C./20 mm Hg, a fraction which contains 2-methylmercapto-4-bromo-anisole as the main component.

EXAMPLE 19

134.5 g (0.8 mol) of dibenzofurane and 125 g (1.6 mols) of dimethylsulphoxide are stirred with 500 ml of anhydrous hydrofluoric acid for 10 hours at 70° C. in an autoclave.

Most of the hydrofluoric acid is then distilled off from the brown homogeneous solution on a boiling water bath, first under normal pressure and then under a waterpump vacuum. The residue is diluted with water to 1.5 l and the solution is clarified with charcoal and completely neutralized hot by adding calcium carbonate incrementally and filtered.

(2-Dibenzofuryl)-dimethyl-sulphonium perchlorate of melting point 206°–208° C. is precipitated from a sample of the filtrate on adding 70% strength aqueous perchloric acid.

150 g of potassium hydroxide are then added to the filtrate and the mixture is boiled for about 3 hours under reflux. The oil which has separated out is extracted with ether. The ether extract gives 125 g of crude product which contains 63.2% of 2-methylmercapto-dibenzofurane (46% of theory) and 28.7% of an unidentified compound.

The crude product is distilled under reduced pressure; the fraction of the distillate which passes over at 175°–185° C./1 mm Hg partially crystallizes directly.

Recrystallization from hexane gives pure 2-methylmercapto-dibenzofurane of melting point 85°–87° C.

EXAMPLE 20

51 g (0.65 mol) of dimethylsulphoxide were added dropwise to a solution, cooled to about 0° C., of 109 g (0.65 mol) of carbazole in 400 ml of hydrofluoric acid and the mixture was then stirred for 16 hours at 20° C.

Hydrogen fluoride was distilled off from the dark green solution and a solid green residue remained which was boiled up with 1 l of water and filtered off hot. This residue (83 g) consisted mainly of carbazole.

70 ml of 70% strength aqueous perchloric acid was added to the filtrate and the yellowish perchlorate which had precipitated was filtered off, washed with water and dried in a desiccator; yield 115 g (23.6% of theory) of carbazole-2,2'-bis-dimethylsulphonium perchlorate, which explodes on impact.

A sample of the perchlorate was decomposed by boiling with dilute sodium hydroxide solution, which gave 2,2'-bismethylmercapto-N-methyl-carbazole of melting point 107°–108° C. (from ethanol).

EXAMPLE 21

78 g of dimethylsulphoxide were added dropwise to a mixture of 128 g (1.0 mol) of naphthalene and 300 ml of anhydrous hydrofluoric acid, while cooling with ice/sodium chloride and stirring; the mixture was then further stirred for 19 hours at room temperature (about 20° C.).

Hydrofluoric acid was then distilled off under normal pressure and 300 ml of chlorobenzene were added to the residue.

The chlorobenzene was then distilled off, hydrofluoric acid still remaining in the residue being distilled off at the same time, and the residue was heated to 180° C. for about 30 minutes.

The oil formed was taken up in ether, whereupon a residue of undecomposed sulphonium chloride remained undissolved.

This undissolved material was taken up in water; precipitation with 70% strength aqueous perchloric acid gave 21.5 g (7.5% of theory) of (1-naphthyl)-dimethyl-sulphonium perchlorate of melting point 143°–145° C.

The ethereal solution was treated with animal charcoal and filtered, the ether was stripped off and the residue was distilled in vacuo.

123 g (71% of theory) of 1-methylmercapto-naphthalene were obtained in the boiling range 160°–165° C./18 mm Hg.

EXAMPLE 22

158 g (1.0 mol) of 2-methoxy-naphthalene and 78 g of dimethylsulphoxide were stirred in 400 ml of anhydrous hydrofluoric acid for 16 hours at 20° C. After the hydrofluoric acid had been distilled off, the green reaction solution was diluted with water to 1.5 l, clarified with charcoal and completely neutralized hot by adding calcium carbonate incrementally and then filtered.

(2-Methoxy-1-naphthyl)-dimethylsulphonium perchlorate of melting point 172°–174° C. was precipitated from a sample of the filtrate on adding 70% strength aqueous perchloric acid.

150 g of potassium hydroxide were added to the filtrate and the mixture was boiled for about 3 hours under reflux. The oil which had separated out was isolated by extraction with ether and distillation of the extract gave 172 g (84% of theory) of 1-methylmercapto-2-methoxy-naphthalene; boiling point 150° C./2 mm Hg.

EXAMPLE 23

78 g of dimethylsulphoxide were added to 178 g (1.0 mol) of technically pure anthracene in 400 ml of anhydrous hydrofluoric acid, while cooling with ice/sodium chloride. The mixture was then stirred for 20 hours at room temperature (about 20° C.). The hydrofluoric acid was then distilled off and the residue was diluted with 1 l of water.

In this procedure, 200 g of highly impure anthracene separated out, which was filtered off and discarded.

22 g of (9-anthranyl)-dimethyl-sulphonium perchlorate were precipitated from the filtrate, on adding 30 ml of 70% strength aqueous perchloric acid, as golden yellow flakes which, on warming slowly, suddenly decompose at about 200° C.

EXAMPLE 24

164.5 g (1.75 mols) of phenol and 136.5 g (1.75 mols) of dimethylsulphoxide were successively introduced into 500 ml of anhydrous hydrofluoric acid at about −10° C., while stirring. The solution was then transferred to a 1.3 l high-grade steel autoclave and stirred for 10 hours at 50° C.

Then, as described in Example 1, the hydrofluoric acid was distilled off, the residue was diluted with water to 1.5 l and the solution was clarified with charcoal, thereafter neutralized hot with calcium carbonate and the calcium fluoride which had precipitated was filtered off hot.

The filter cake was washed several times with hot water and the wash water was combined with the filtrate.

A sample of the filtrate gave, on adding perchloric acid, a precipitate of (4-hydroxyphenyl)-dimethyl-sulphonium perchlorate of melting point 155° C.

The filtrate contained the sulphonium salt as an internal phenolate, which was converted into (4-hydroxyphenyl)-dimethylsulphonium chloride by an amount of aqueous hydrochloric acid equivalent to the phenol employed. The solution was then evaporated to dryness, the crystalline residue was suspended in 350 ml of xylene and the xylene suspension was heated to the boil for about 2 hours under reflux, whereupon the salt was decomposed, with the splitting off of methyl chloride, and dissolved.

The solution was then clarified with bleaching earth, the toluene was stripped off and the residue was distilled.

206 g of 4-methylmercapto-phenol (84% of theory) was obtained, in the boiling range 117°–120° C./1.5 mm Hg, as the distillate, which solidified to a solid of melting point 81°–82° C.

EXAMPLES 25–36

In each case equimolar amounts of a phenol and dimethylsulphoxide were successively introduced into the amount of anhydrous hydrofluoric acid indicated at about −10° C. The reaction mixture was then stirred in a 1.3 l high-grade steel autoclave for the number of hours indicated at the temperature indicated.

The hydrofluoric acid was then distilled off as described in Example 1, the residue remaining was diluted with water to 1.5 l and this solution was clarified with charcoal and then neutralized with calcium carbonate under the influence of heat.

The calcium fluoride which had precipitated was filtered off hot and the filter cake was washed thoroughly with several portions of hot water.

Aqueous 70% strength perchloric acid was added to a sample of the filtrate, whereupon the corresponding sulphonium fluoride was precipitated.

The amount of aqueous hydrochloric acid equivalent to the phenol employed was added to the filtrate and the mixture was evaporated to dryness. The residue was either suspended in the solvent indicated, the mixture heated to the boil until the residue dissolved and the solution formed then clarified with bleaching earth, the solvent stripped off and the remaining residue distilled; or the residue was heated to about 130° C. to 150° C. undiluted until the evolution of methyl chloride had ceased, and the remaining residue distilled.

In Table II which follows there are indicated
1. Number of the example
2. Nature and amount in mols of the phenol employed
3. Volume of anhydrous hydrofluoric acid
4. Reaction time and temperature
5. Melting point of the sulphonium perchlorate obtained
6. Solvent for the decomposition of the sulphide
7. Sulphide obtained
8. Its yield in % of theory and
9. Boiling point during the distillation and also
10. Melting point.

Table II

| 1. | 2. | 3. ml | 4. hours | 4. °C | 5. °C | 6. | 7. | 8. | 9. °C/mm Hg | 10. |
|---|---|---|---|---|---|---|---|---|---|---|
| 25 | p-cresol | 1.5 500 | 10 | 70 | | xylene | (2-hydroxy-5-methyl-phenyl)-methyl sulphide | 74.5 | 90–92/2 | |
| 26 | o-cresol | 1.0 300 | 20 | 20 | 133–135 | o-dichloro-benzene | (4-hydroxy-3-methyl-phenyl)-methyl sulphide | 60 | 119–122/2 | about 37 |
| 27 | 4-methoxy-phenol | 1.5 500 | 10 | 60 | 147–148 | xylene | (2-hydroxy-5-methoxy-phenyl)-methyl sulphide | 58.5 | 117–122/1 | 49–50 |
| 28 | 3-methoxy-phenol | 1.5 500 | 10 | 50 | 149–131 | xylene | (2-hydroxy-4-methoxy-phenyl)-methyl sulphide | 46 | 112–118/1.5 | |
| | | | | | 193–195 | | (4-hydroxy-2-methoxy-phenyl)-methyl sulphide | 28 | 161–165/1.5 | 94–96 |
| 29 | 4-chloro-phenol | 1.5 500 | 10 | 60 | 167–168 | | (5-chloro-2-hydroxy-phenyl)-methyl sulphide | 47 | 90–96/1.5 | 36–38 |
| 30 | 3-chloro-phenol | 1.5 500 | 10 | 60 | 132–134 | | (2-chloro-4-hydroxy-phenyl)-methyl sulphide | 64 | 142/1.5 | 66–67 |

Table II-continued

| 1. | 2. | 3. ml | 4. hours | 4. °C | 5. °C | 6. | 7. | 8. | 9. °C/mm Hg | 10. |
|---|---|---|---|---|---|---|---|---|---|---|
| | | | | | | | (4-chloro-2-hydroxy-phenyl)-methyl sulphide | 8.5 | Note 1 | |
| 31 | 2-chloro-phenol | 1.5 | 500 | 10 | 60 | 148–150 | | (3-chloro-2-hydroxy-phenyl)-methyl sulphide | 69 | 105–107/1.5 | |
| 32 | 4-tert.-butylphenol | 1.5 | 500 | 10 | 50 | 167–168 | | (2-hydroxy-5-tert.-butyl-phenyl)-methyl sulphide | 61 | 108–112/1 | |
| 33 | 3,5-dimethyl-phenol | 1.0 | 300 | 170 | 20 | | | (2-hydroxy-4,6-dimethyl-phenyl)-methyl sulphide | 47 | 90–100/2 | |
| | | | | | | | (4-hydroxy-2,6-dimethyl-phenyl)-methyl sulphide | 26 | 129–132/2 | |
| 34 | hydroquinone | 1.0 | 300 | 17 | 20 | 182–184 | xylene | (2,5-dihydroxyphenyl)-methyl sulphide | 88 | | 81–82 |
| 35 | resorcinol | 1.4 | 500 | 10 | 50 | 145–147 | xylene | (2,4-dihydroxyphenyl)-methyl sulphide | 78 | 136–142/1.5 | |
| 36 | pyrocatechol | 1.0 | 300 | 20 | 20 | 190–193 | o-dichloro-benzene | (3,4-dihydroxyphenyl)-methyl sulphide | 82 | 163–165/1.5 | 50–52 |

Note 1:
The compound was separated off by column chromatography and obtained as an oil.

EXAMPLE 37

117 g (1.5 mols) of dimethylsulphoxide were added dropwise to a solution, cooled to 0° C., of 162 g (1.5 mols) of m-cresol and 81 g (0.75 mol) of p-cresol in 500 ml of anhydrous hydrofluoric acid, while stirring. The solution was then stirred for 10 hours at 70° C. The hydrofluoric acid was then distilled off and the residue was diluted with 1.5 l of water. The unreacted cresol which had separated out was isolated by extraction with methylene chloride, which gave 97 g of a mixture of 11.7% of m-cresol and 88.3% of p-cresol.

The aqueous solution was then neutralized hot with calcium carbonate, the calcium fluoride which had separated out was filtered off and 125 ml of concentrated hydrochloric acid was added to the filtrate until it gave a clearly acid reaction and the mixture was then evaporated.

The crystalline residue which remained was suspended in 500 ml of xylene and the suspension was heated under reflux until the evolution of methyl chloride had ended. Thereafter the xylene solution was clarified with bleaching earth and, after filtration, concentrated.

This gave 232 g of a residue which, in addition to 10% of xylene, contained 26.6% of (2-hydroxy-4-methyl-phenyl)-methyl sulphide and 61.8 of (4-hydroxy-2-methyl-phenyl)-methyl sulphide, corresponding to a total yield of the mixture of o- and p-methylmercapto-substituted m-cresols of 88.5% of theory, relative to m-cresol employed.

EXAMPLE 38

78 g of dimethylsulphoxide were added dropwise to a solution of 144 g (1.0 mol) of 2-naphthol in 400 ml of anhydrous hydrofluoric acid at about −10° C., while stirring, and the reaction mixture was further stirred for 16 hours at 20° C.

The hydrofluoric acid was then distilled off and the residue was diluted with 2 l of water.

The solution was clarified with charcoal and neutralized by adding potassium hydroxide in portions.

During this procedure a salt-like reaction product separated out, probably (2-hydroxy-1-naphthyl)-dimethyl-sulphonium hydroxide, which was filtered off and dried at 120° C. in a vacuum drying cabinet to constant weight.

During this procedure, the substance lost its salt-like character with the release of water and an internalsulphonium naphtholate having the emperical formula $C_{12}H_{12}OS$ of melting point 168°–170° C. was formed; the yield was almost quantitative.

A sample of this substance was dissolved in water and 70% strength aqueous perchloric acid was added, whereupon (2-hydroxy-1-naphthyl-)-dimethyl-sulphonium perchlorate of melting point 197°–199° C. was precipitated.

175 g (0.86 mol) of the sulphonium naphtholate obtained as described above were suspended in 800 ml of water and 75 ml of concentrated hydrochloric acid were added, a solution being formed.

The solution was clarified with charcoal and evaporated to dryness. On further heating the evaporation residue up to a final temperature of 150° C., methyl chloride was given off.

This gave, after about 2 hours, 156 g of an oil as the residue, which contained 98% of (2-hydroxy-1-naphthyl)-methyl sulphide, corresponding to a yield of 93.5% of theory.

The substance boils at 143° C./3 mm Hg.

EXAMPLE 39

202 g (1.0 mol) of 2,4,4'-trihydroxy-diphenyl were stirred with 78 g of dimethylsulphoxide in 500 ml of anhydrous hydrofluoric acid for 10 hours at 50° C. The hydrofluoric acid was then evaporated off in a boiling water bath, first under normal pressure and then under a waterpump vacuum, and the remaining residue was thoroughly stirred, after cooling, with a mixture of acetone and diethyl ether in a ratio of about 1:1. This gave [5-(4-hydroxyphenyl)-2,4-dihydroxyphenyl]-dimethyl-sulphonium fluoride as a crystalline substance; yield 210 g (75% of theory). On heating, the substance gradually decomposes without melting.

Analysis: $C_{14}H_{15}FO_3S$. found: 59.0/59.3% C 5.5% H 16.6/16.6% O 10.9/11.0% S found: 59.6 C 5.2 H 17.0 O 11.3 S.

Recrystallizing a sample of the fluoride from half-concentrated hydrochloric acid gave the corresponding sulphonium chloride; it melts, with decomposition, at 165° C.

A sample of the chloride was decomposed by boiling in trichlorobenzene. On cooling, colorless needles of 2,4,4'-trihydroxy-5-methylmercapto-diphenyl of melting point 220°–222° C. crystallized out of the solution.

EXAMPLE 40

300 ml of ice-cold anhydrous hydrofluoric acid were poured over a mixture, cooled to 0° C., of 54 g (0.5 mol) of anisole and 70 g (0.5 mol) of phenyl-methyl-sulphoxide. The mixture was then stirred for 16 hours at room temperature (about 20° C.).

The majority of the hydrofluoric acid was stripped off, at 100° C./100 mm Hg, from the reddish solution formed and the residue, a light yellow oil, was taken up in 1 l of water.

The solution was neutralized with solid potassium hydroxide, a further 60 g of potassium hydroxide were added and the mixture was boiled for 2 hours under reflux.

The oil which had separated out was isolated by extraction with methylene chloride.

The crude product (101.5 g) contained 96.8% of 4-methoxy-diphenyl sulphide of boiling point 155°–165° C./3 mm Hg, corresponding to a yield of 91% of theory.

EXAMPLE 41

300 ml of ice-cold anhydrous hydrofluoric acid were poured over 70.5 g (0.75 mol) of phenol and 105 g (0.75 mol) of phenyl-methyl sulphoxide and the mixture was stirred for 16 hours at room temperature. The majority of the hydrofluoric acid was stripped off from the resulting solution at 100° C./100 mm Hg and the residue was diluted with 800 ml of water.

The aqueous solution was neutralized with 45% strength by weight aqueous sodium hydroxide solution and the sodium fluoride which had separated out was filtered off. The filtrate was then adjusted to a pH of 4–5 with concentrated hydrochloric acid and, after adding 300 g of sodium chloride, the mixture was boiled for about 5 hours under reflux until the evolution of methyl chloride had ceased.

Extraction of the aqueous solution with ether gave 145 g of crude product which, according to analysis by gas chromatography, contained 90.1% of 4-hydroxy-diphenyl sulphide, corresponding to a yield of 86.5% of theory; the substance distils at 180° to 183° C./2.5 mm Hg.

EXAMPLE 42

52 g (0.5 mol) of tetrahydrothiophenoxide were added dropwise to a solution of 79 g (0.5 mol) of 1,2-dimethoxybenzene in 200 ml of anhydrous hydrofluoric acid at −10° C. The solution was then stirred for 18 hours at room temperature.

A sample of the pale yellow reaction solution was then diluted with water and 70% strength aqueous perchloric acid was added, whereupon (3,4-dimethoxy-phenyl)-tetramethylenesulphonium perchlorate of melting point 195°–197° C. precipitated.

Most of the hydrofluoric acid was then blown out of the reaction solution with air on a boiling water bath. The remaining residue was diluted with water to 1 l, neutralized with potassium hydroxide solution and, after adding 100 g of potassium hydroxide, boiled for 2 hours under reflux.

The oil which thereby separated out was isolated by extraction with methylene chloride.

Distillation of 118 g of crude product gave 28 g (25% of theory) of (3,4-dimethoxy-phenyl)-but-3-enyl sulphide; boiling point 126°–128° C./1.5 mm Hg, 31 g (25.5% of theory) of (3,4-dimethoxy-phenyl)-(4-hydroxy-butyl) sulphide; boiling point 192° C./1.5 mm Hg, and 52 g (44.5% of theory) of bis-4,4′-(3,4-dimethoxy-phenylmercapto)-butyl ether which remained as the distillation residue at 1.5 mm Hg; it was purified by chromatography on silica gel.

EXAMPLE 43

52 g (0.5 mol) of tetrahydrothiophenoxide were added dropwise to a solution of 53 g (0.5 mol) of m-xylene in 300 ml of anhydrous hydrofluoric acid at −10° C. The solution was then stirred for 18 hours at room temperature.

A sample of the reaction solution was then diluted with water and perchloric acid was added, whereupon (2,4-dimethylphenyl)-tetramethylene-sulphonium perchlorate of melting point 120°–122° C. was precipitated.

The hydrofluoric acid was distilled off from the resulting reaction solution and the remaining residue was dissolved with water, to a volume of 1 l. The solution was clarified with charcoal and neutralized with calcium carbonate and the calcium fluoride which had precipitated was filtered off.

60 g of morpholine were added to the neutral filtrate and the solution was boiled for 3 hours under reflux.

The reaction product was isolated by ether extraction and subsequent distillation of the extract gave 67 g of 1-(2,4-dimethyl-phenylmercapto)-4-(N-morpholino)-butane (48% of theory) in the boiling range 181°–186° C./1.5 mm Hg.

EXAMPLE 44

61 g (0.5 mol) of 4-methoxy-toluene and 52 g (0.5 mol) of tetrahydrothiophenoxide were reacted in 300 ml of anhydrous hydrofluoric acid for 20 hours at 20° C., while stirring.

Thereafter a sample of the solution gave, after dilution with water, a precipitate of (2-methoxy-5-methyl-phenyl)-tetramethylene-solphonium perchlorate of melting point 97° C. on adding perchloric acid.

The hydrofluoric acid was then distilled off from the reaction solution and the remaining residue was dissolved with water, to a volume of 1 l. The solution was clarified with charcoal and neutralized with calcium carbonate and the calcium fluoride was filtered off. 70 g of sodium phenolate were then added to the neutral solution of the sulphonium fluoride and the solution was boiled for about 3 hours under reflux.

The reaction product was then isolated by extraction with methylene chloride and distilled in vacuo.

This gave 30 g (26.5% of theory) of (2-methoxy-5-methyl-phenyl)-(4-hydroxy-butyl) sulphide in the boiling range 174°–177° C./1.5 mm Hg and 64 g (42% of theory) of (2-methoxy-5-methyl-phenyl)-(4-phenoxybutyl) sulphide in the boiling range 220°–225° C./1.5 mm Hg; this compound melts at 59°–61° C. when crystallized from hexane.

EXAMPLE 45

69 g (0.5 mol) of 1,4-dimethoxybenzene were stirred in 300 ml of anhydrous hydrofluoric acid with 52 g of tetrahydrothiophoenoxide for 18 hours at room temperature (about 20° C.).

(2,5-Dimethoxy-phenyl)-tetramethylene-sulphonium perchlorate of melting point 116°–118° C. was then precipitated from a sample of the reaction solution with perchloric acid.

The hydrofluoric acid was distilled off from the reaction solution and the remaining residue was dissolved with water, to a volume of 1 l. The solution was clarified with charcoal and neutralized with calcium carbonate and the calcium fluoride which had precipitated was filtered off.

30 g of potassium cyanide were then added to the neutral, aqueous sulphonium fluoride solution and the mixture was boiled for 2 hours under reflux. The reaction product was isolated by extraction with ether.

This gave 73 g (56% of theory) of 5-(2,5-dimethoxy-phenylmercapto)-valeronitrile; melting point 64°–66° C. (from cyclohexane).

EXAMPLE 46

52 g (0.5 mol) of tetrahydrothiophenoxide were added dropwise to a solution of 79 g (0.5 mol) of 2-methoxynaphthalene in 300 ml of anhydrous hydrofluoric acid at about −10° C. The reaction mixture was then stirred for 20 hours at 20° C.

(2-Methoxy-1-naphthyl)-tetramethylene-sulphonium perchlorate of melting point 230° C. (decomposition) was precipitated from a sample of the green reaction solution on adding perchloric acid.

The hydrofluoric acid was then distilled off from the reaction mixture at 100° C./40 mm Hg and the residue was diluted with water, to a volume of 1 l. The solution was neutalized with calcium carbonate and the calcium fluoride which had precipitated was filtered off.

The water was distilled off from the filtrate and the residue was heated further to 150° C. in an oil bath until a sample taken was soluble in ether to give a clear solution.

Distillation in vacuo of the oily residue of 110 g thus obtained gave about 77 g of 1-fluoro-4-(2-methoxy-1-naphthylmercpato)-butane (58% of theory) in the boiling range 108°–110° C./1.5 mm Hg.

About 27.5 g of 1,4-bis-(2-methoxy-1-naphthylmercapto)butane (25% of theory) remained as the residue; melting point 90°–91° C. (from benzene/hexane).

EXAMPLE 47

52 g (0.5 mol) of tetrahydrothiophenoxide were added dropwise to a solution of 54 g (0.5 mol) of p-cresol in 300 ml of anhydrous hydrofluoric acid, while cooling with ice/sodium chloride. The reaction solution was then further stirred for 17 hours at 20° C.

(2-Hydroxy-5-methyl-phenyl)-tetramethylene-sulphonium perchlorate of melting point 156°–157° C. was precipitated from a sample of the reaction solution on adding perchloric acid.

The hydrofluoric acid was then distilled off from the reaction solution and the remaining residue was diluted with water to 1 l and the solution was neutralized with calcium carbonate and filtered off from the calcium fluoride which had precipitated.

About 50 ml of concentrated hydrochloric acid were added to the filtrate and the mixture was concentrated to 250 ml. 64 g of sulphonium chloride thereby separated out and were filtered off.

The sulphonium chloride thus obtained was heated to about 110°–120° C. for 5 hours, whereupon an oil soluble in ether was formed which, according to analysis by NMR spectroscopy, was 1-chloro-4-(2-hydroxy-5-methyl-phenylmercapto)butane; yield: 54 g (47% of theory). The substance decomposed during the attempt to distil it.

EXAMPLE 48

52 g (0.5 mol) of tetrahydrothiophenoxide were added dropwise to a mixture of 72 g (0.5 mol) of 2-naphthol in 200 ml of anhydrous hydrofluoric acid, while cooling with ice/sodium chloride, and the reaction mixture was then further stirred for 20 hours at 20° C.

The majority of the hydrogen fluoride was then blown out with air and the residue was taken up in 1 l of water.

(2-Hydroxy-1-naphthyl)-tetramethylene-sulphonium perchlorate of melting point 160°–162° C. was precipitated from a sample of the solution with perchloric acid.

The aqueous solution was then rendered strongly alkaline with potassium hydroxide and the precipitate which had separated out, probably an intramolecular sulphonim naphtholate, was filtered off.

The precipitate was then suspended in 1 l of water and dissolved by adding 40 ml of concentrated hydrochloric acid dropwise. The solution was clarified with charcoal, the water was completely evaporated off and the residue was heated to 110°–120° C. for 2 hours in an oil bath. The remaining residue was an oil which could not be distilled without decomposition.

Yield: 99 g of 1-chloro-4-(2-hydroxy-1-naphthylmercapto)-butane (74.5% of theory); the resulting compound was pure and uniform according to analysis by thin layer chromatography and the NMR spectrum corresponded to the structure indicated.

It will be appreciated that the instant specification and claims are set forth by way of illustration and not limitation, and that various modifications and changes may be made without departing from the spirit and scope of the present invention.

What is claimed is:

1. A process for the production of an arylsulphonium fluoride, comprising reacting an aromatic compound of the formula

in which Ar is an aromatic radical with a sulphoxide of the formula

in which $R^1$ and $R^2$ each independently is an aliphatic or aromatic radical or, together, a divalent radical, in the presence of hydrogen fluoride.

2. A process according to claim 1, in which the compound Ar—H is a compound of the formula

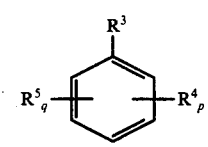

in which $R^3$ and $R^4$ each independently is a hydroxyl group or an alkyl, aryl, alkoxy, aroxy, alkylthio or arylthio radical, each $R^5$ independently is a halogen atom or an alkyl radical, p and q each independently is 0, 1 or 2, and $R^3$ and one or both of adjacent radicals $R^4$ and $R^5$ can together form a fused, cycloaliphatic or aromatic 5-membered or 6-membered ring.

3. A process according to claim 1, in which the sulphoxide is dimethylsulphoxide, diethylsulphoxide, methylphenylsulphoxide, -(p-tolyl)-methyl-sulphoxide, (p-anisyl)-methylsulphoxide, (p.tert.butyl-phenyl)-ethylsulphoxide or tetrahydrothiophenoxide.

4. A process according to claim 1, in which the hydrofluoric acid has a hydrogen fluoride content of at least about 90% by weight.

5. A process according to claim 1, in which the hydrofluoric acid has a hydrogen fluoride content of at least about 95% by weight.

6. A process according to claim 1, in which about 2 to 10 parts of hydrofluoric acid are used per part by weight of the aromatic compound.

7. A process according to claim 1, in which about 2 to 5 parts of hydrofluoric acid are used per part by weight of the aromatic compound.

8. A process according to claim 1, in which the reaction is carried out at a temperature from about −80° to 150° C.

9. A process according to claim 3, in which the aromatic compound is at least one of toluene, o-, m- and p-xylene, naphthalene, α- and β-mono-and di-methyl and -ethyl-naphthalenes, anthracene, diphenyl, diphenylmethane, tetralin, indane, phenol, o-, m- and p-cresol, butylphenol, xylenol, resorcinol, pyrocatechol, hydroquinone, α- and β-naphthol, anisole, hydroquinonedimethyl ether, pyrocatechol monomethyl ether, α- and β-methoxynaphthalene, thioanisole, 4-hydroxy-thioanisole, o-, m- and p-chlorophenol, diphenyl ether, dibenzofurane, carbazole, acenaphthene, fluorene, cumene, mesitylene and o-, m-and p-cymene, the hydrofluoric acid has a hydrogen fluoride content of at least about 95% by weight, about 2 to 5 parts of hydrofluoric acid are used per part by weight of the aromatic compound and the reaction is carried out at a temperature of from about −80° to 150° C.

* * * * *